United States Patent [19]

Gambale et al.

[11] Patent Number: 5,144,959
[45] Date of Patent: Sep. 8, 1992

[54] CATHETER GUIDEWIRE WITH VARYING RADIOPACITY

[75] Inventors: Richard A. Gambale, Tyngsboro, Mass.; James F. Crittenden, Hollis, N.H.; L. Venkata Raman, Framingham, Mass.

[73] Assignee: C. R. Bard, Inc., Murray Hill, N.J.

[21] Appl. No.: 394,075

[22] Filed: Aug. 15, 1989

[51] Int. Cl.[5] ............................................ A61M 10/00
[52] U.S. Cl. .................................. 128/772; 128/657; 604/170
[58] Field of Search ................... 128/772, 657, 658; 604/164, 170

[56] References Cited

U.S. PATENT DOCUMENTS

| 3,749,086 | 7/1973 | Kline et al. | |
|---|---|---|---|
| 4,545,390 | 10/1985 | Leary | 128/772 |
| 4,619,274 | 10/1986 | Morrison | 128/657 |
| 4,719,924 | 1/1988 | Crittenden | 128/772 |
| 4,748,986 | 6/1988 | Morrison et al. | 128/772 |
| 4,763,647 | 8/1988 | Gambale | 128/772 |
| 4,773,432 | 9/1988 | Rydell | 128/772 |
| 4,796,637 | 1/1989 | Mascuch et al. | 128/658 |
| 4,846,193 | 7/1989 | Tremulis et al. | 128/772 |
| 4,867,173 | 9/1989 | Leoni | 128/772 |
| 4,878,492 | 11/1989 | Sinofsky et al. | 606/13 |
| 4,921,482 | 5/1990 | Hammerslag et al. | 128/772 |
| 4,922,924 | 5/1990 | Gambale et al. | 128/772 |
| 4,928,693 | 5/1990 | Goodin et al. | 128/772 |
| 4,953,553 | 9/1990 | Tremulis | 128/772 |
| 4,991,602 | 2/1991 | Amplatz et al. | 128/657 |

FOREIGN PATENT DOCUMENTS 0274412  7/1988  European Pat. Off. .

Primary Examiner—Stephen C. Pellegrino
Assistant Examiner—Ralph A. Lewis
Attorney, Agent, or Firm—Wolf, Greenfield & Sacks

[57] ABSTRACT

A guidewire for use with a catheter has varying radiopacity in its distal end. In one embodiment the guidewire includes a shaft having an outer helical coil attached to the distal region of the shaft, the coil extending distally beyond the distal end of the shaft and terminating in a tip weld. A smaller diameter inner helical coil is disposed within the outer coil and is attached at its proximal end to the distal end of the shaft and at its distal end to the tip weld. The inner coil is formed from a highly radiopaque material. The portion of the shaft contained within the outer coil is plated thinly with a highly radiopaque material. When viewed under fluoroscopy, the highly radiopaque coil will define a dark image whereas the more proximal plated portion of the shaft will define a moderately radiopaque image. In other embodiments, the coil at the distal end of the catheter is variously electroplated to provide regions of high radiopacity, moderate radiopacity and relatively no radiopacity.

6 Claims, 3 Drawing Sheets

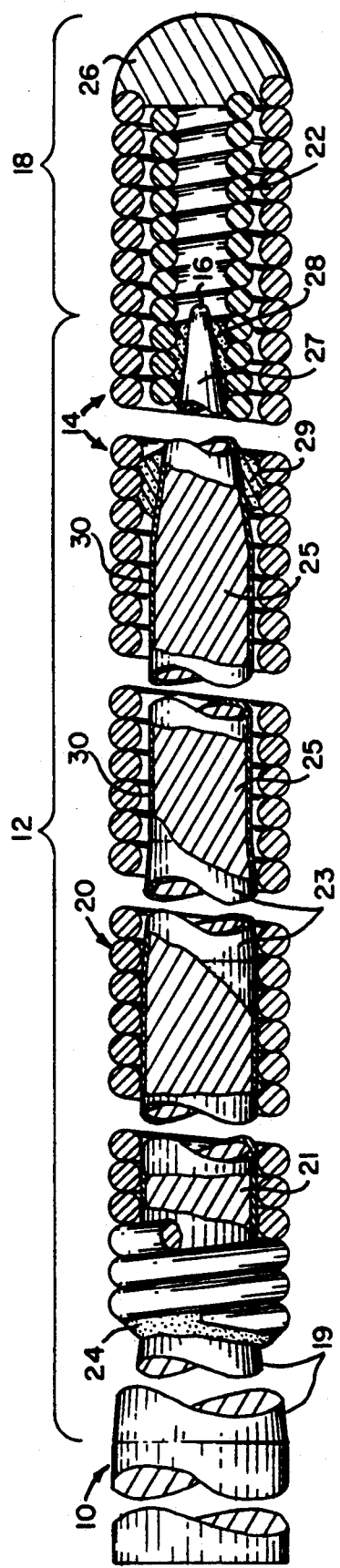
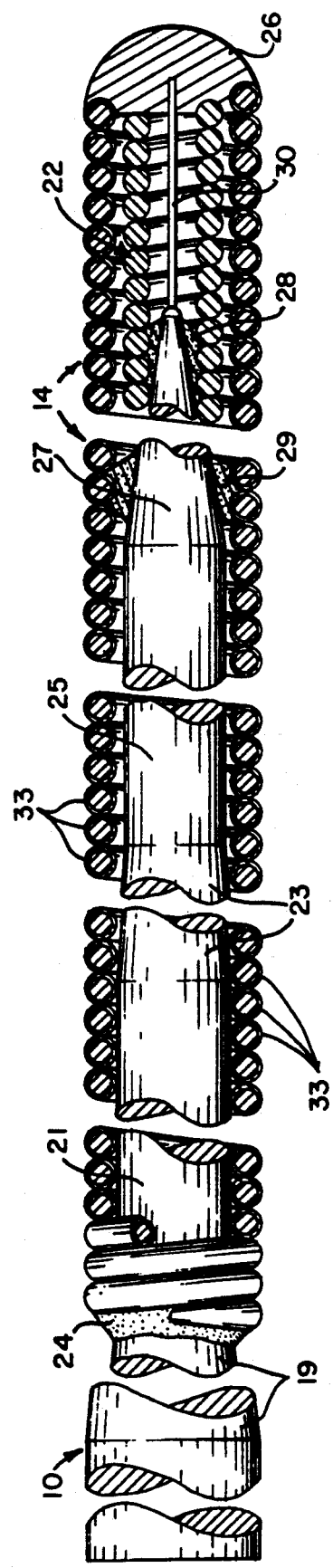
Fig. 1
Fig. 2

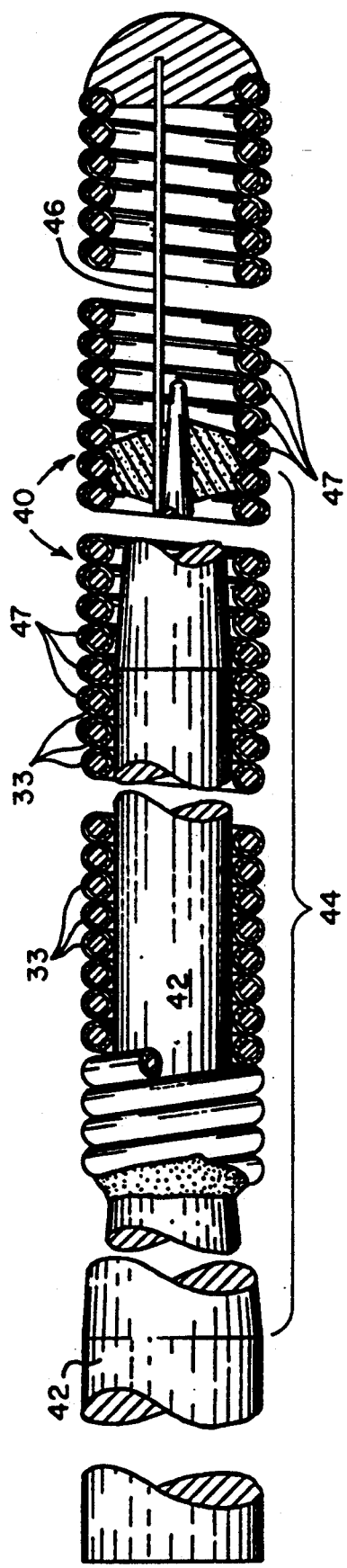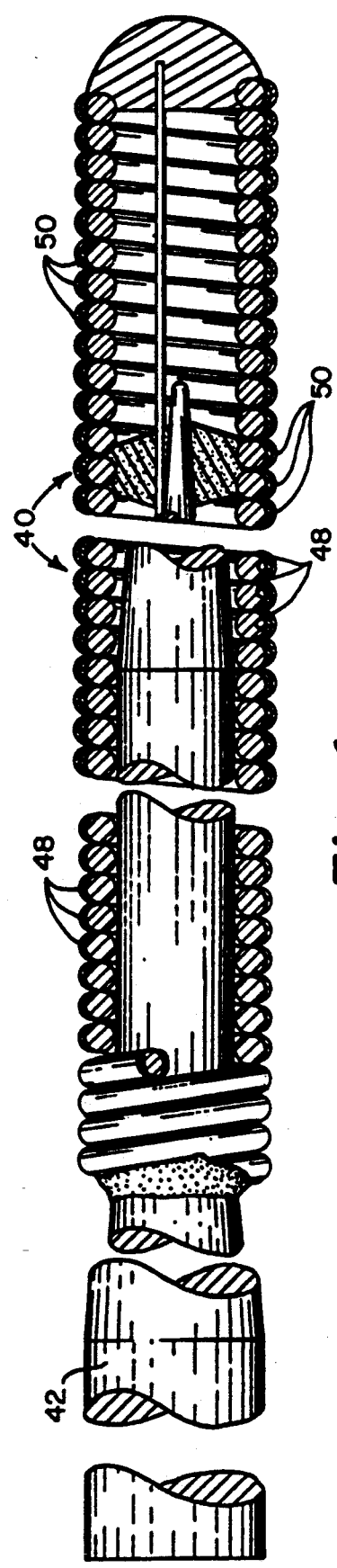

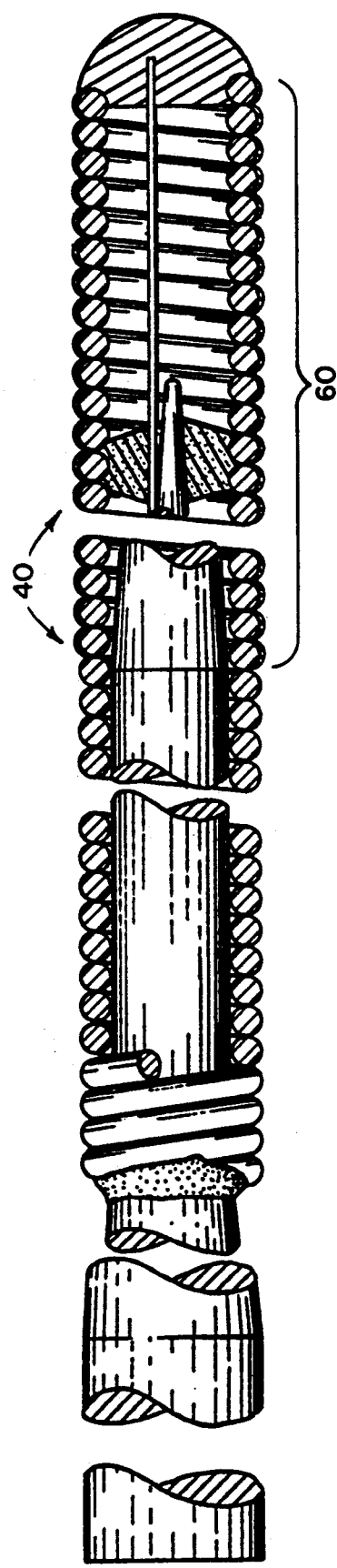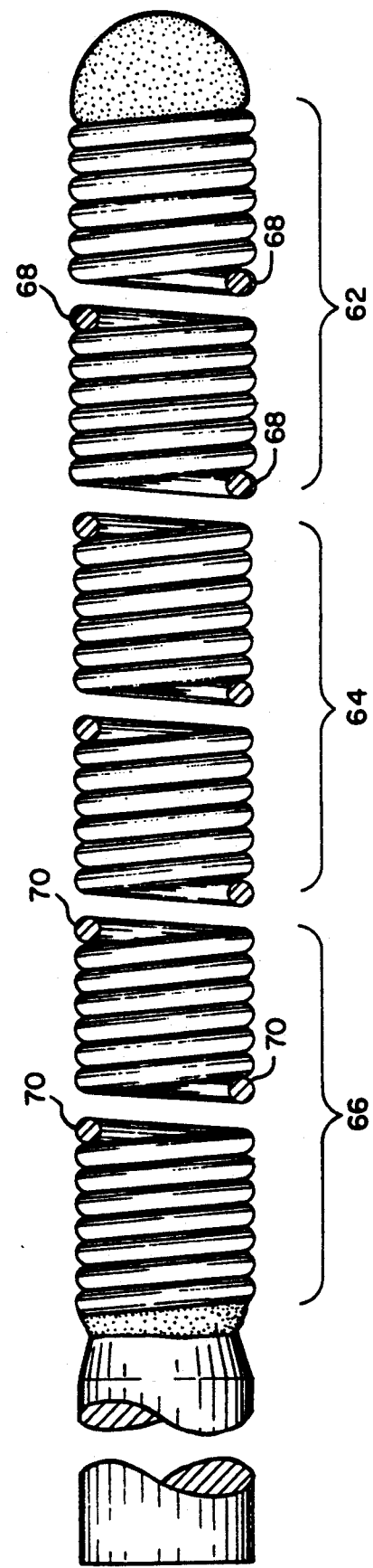

CATHETER GUIDEWIRE WITH VARYING RADIOPACITY

FIELD OF THE INVENTION

The invention relates to guidewires used to support and guide catheters as they are advanced through body lumens such as blood vessels.

BACKGROUND OF THE INVENTION

A wide variety of guidewires are used for various medical purposes in the treatment of the human body. Among the more common uses is in blood vessels to guide a catheter to a site within the patient's blood vessel to perform the procedure for which the catheter is adapted. For example, guidewires, particularly small diameter steerable guidewires, perform an important function in percutaneous transluminal coronary angioplasty. Illustrative of such guidewires are those described in U.S. Pat. No. 4,545,390 (Leary) and U.S. Pat. No. 4,538,622. Each of the guidewires described in those patents has a torsionally rigid, longitudinally flexible shaft and a flexible distal portion that includes a coil, all or part of which is radiopaque so that the physician can monitor fluoroscopically the position and advancement of the guidewire in the patient's blood vessel. In procedures, such as coronary angioplasty, in which a catheter is advanced through the patient's arteries, it often is the practice to inject a radiopaque contrast liquid into the artery so that the shape and paths of the artery may be visualized fluoroscopically. The radiopacity of the guidewire coil may be so dense as to visually obstruct part of the artery which the physician may desire to view when the contrast liquid is injected. For use in such instances, it would be desirable for the guidewire to be only partially radiopaque, that is, to form a light but visible grey shadow in some portions, a heavy, dark fluoroscopic image on another portion and in some cases an additional non-radiopaque portion.

It is among the general object of the invention to provide guidewires having the foregoing desirable characteristics.

SUMMARY OF THE INVENTION

In accordance with one embodiment of the invention, a guidewire has an elongate flexible shaft with a tapered distal portion. A helical coil formed from a relatively low radiopacity metal is mounted on the distal end of the shaft over the tapered portion, the tapered portion being received in and extending through the coil. The distal end of the tapered portion terminates short of the distal end of the coil and another, smaller diameter coil is attached to and extends distally from the distal end of the shaft. The distal end of the inner coil and outer coil are attached to a tip weld at the distal tip of the guidewire. The inner coil is formed from a highly radiopaque material that will appear dark under fluoroscopy. A region of the guidewire proximal of the inner coil is rendered moderately radiopaque by plating the tapered portion of the shaft with a thin layer of a highly radiopaque material. Thus, the guidewire provides a distal coil having a highly radiopaque distal segment and a moderately radiopaque proximal segment which will not completely obstruct visualization of arteries into which radiopaque contrast liquid has been injected.

In another embodiment of the invention, the inner coil is formed from a highly radiopaque metal while the outer coil is formed from a non-radiopaque material. In this embodiment, the tapered portion of the shaft remains unplated. Instead, the outer coil is plated thinly with a highly radiopaque material. This arrangement also results in a guidewire having highly radiopaque and moderately radiopaque segments.

In a further embodiment, a single helical coil is attached to the distal end of a guidewire shaft. The coil is formed from an alloy having moderate radiopacity. The tip portion of the coil is plated with a highly radiopaque material. In a modification of this embodiment, the single coil may be formed from a non-radiopaque material and may be plated in two sections, including a distal tip section that is heavily plated with radiopaque material and a more proximal coil segment which is only moderately plated with radiopaque material.

In a still further modification of this embodiment, the coil is formed from a material that is moderately radiopaque and a distal tip section is plated with additional radiopaque material to define a deeply radiopaque distal section and a moderately radiopaque proximal section under fluoroscopy.

Still another embodiment relates to a guidewire having coil segments that are highly radiopaque, moderately radiopaque and non-radiopaque. In the illustrated version of this embodiment, a distal segment of the helical coil is highly radiopaque, an intermediate segment is non-radiopaque and a proximal segment is moderately radiopaque. The wire is intended to be used so that the non-radiopaque segment is placed within the stenosed region of the artery so that the radiopacity of the guidewire will not interfere with the radiopaque imaging of the stenosis when the artery is flooded with radipaque contrast liquid.

It is among the objects of the invention to provide a guidewire having a coil assembly at its distal end in which the region of the coil assembly includes a highly radiopaque distal segment and a moderately radiopaque proximal segment.

DESCRIPTION OF THE DRAWINGS

The foregoing and other objects and advantages of the invention will be appreciated more fully from the following further description thereof, with reference to the accompanying drawings wherein:

FIG. 1 is a longitudinal sectional fragmented illustration of one embodiment of the invention;

FIG. 2 is a longitudinal sectional fragmented illustration of another embodiment of the invention;

FIG. 3 is a longitudinal sectional fragmented illustration of a further embodiment of the invention;

FIG. 4 is a longitudinal sectional fragmented illustration of yet another embodiment of the invention;

FIG. 5 is a longitudinal sectional fragmented illustration of a still further embodiment of the invention; and FIG. 6 is a fragmented illustration of another embodiment of the invention.

DESCRIPTION OF THE ILLUSTRATIVE EMBODIMENT

As illustrated in FIG. 1, the guidewire includes an elongated rotationally rigid, longitudinally flexible shaft 10 having a tapered region 12 at its distal end. A coil assembly 14 is mounted to the distal end of the shaft, the tapered region 12 of the shaft 10 extending into and being received within the coil assembly 14. The distal tip 16 of the shaft 10 terminates short of the distal end of the coil assembly 14 to define a flexible tip portion 18.

The guidewire may have an overall length of the order of 175 cm, with the distal region 12 of the shaft extending over approximately 30 cm. The flexible tip portion 18 may extend over approximately 2 cm length. The tapered region 12 may be formed in a step taper, as shown, having a first tapered segment 19, about 3 cm long, which merges into a barrel segment 21, about 0.008" diameter. Segment 21 is about 14 cm long and merges into a second tapered segment 23, about 3 cm long which, in turn, merges into another barrel segment 25, about 0.006" diameter. The barrel segment 25 merges into a distal tip taper segment 27, about 4 cm long, which tapers to about 0.002" diameter.

The coil assembly 14 includes an outer helical coil 20 and an inner helical coil 22. The outer coil 20 is formed from a material that is relatively lightly radiopaque, such as stainless steel wire having a diameter of the order of 0.003". The outer coil 20 is attached to the shaft 10 at a proximal brazed joint 24 and at a distal brazed joint 29. The outer coil 20 extends distally beyond the distal end 16 of the shaft 10. The distal end of the outer coil 20 terminates in a hemispherical tip weld 26. The inner helical coil 22 is formed from a highly radiopaque material, such as a gold-platinum alloy. It is attached at its proximal end to the distal end 16 of tapered segment 27 of the shaft 10 at an inner brazed joint 28, the outermost end of the inner helical coil 22 is attached to the tip weld 26. The tapered region 12 of the shaft 10 is lightly plated as indicated at 30 with a highly radiopaque material such as gold. The gold plating may be of the order of 0.0001" thick. The plating is illustrated in the drawing, highly exaggerated in thickness for purposes of illustration. The plating is such that under fluoroscopy, the region 12 of the guidewire will appear less radiopaque than the region 18.

Thus, when viewed on a fluoroscope, the guidewire will exhibit a heavy dark distal portion and a moderately shadowed proximal portion. The moderately shadowed proximal portion permits visualization of the portion of the blood vessel in which it is contained when the blood vessel is injected with radiopaque contrast liquid.

In addition, the foregoing embodiment of the invention incorporates a construction in which the distal tip region 18 presents a highly flexible atraumatic tip.

FIG. 2 illustrates another embodiment of the invention which is somewhat similar in construction to that shown in FIG. 1, like reference characters for like elements being incorporated into both FIGS. 1 and 2. In this embodiment, the inner helical coil 22 also is formed from a highly radiopaque material. The tapered region 12 of the shaft 10, however, is unplated. Instead, the wire from which the outer coil 20 is formed is plated thinly with a highly radiopaque material as indicated at 33. Thus, the highly radiopaque inner coil defines a dark region under the fluoroscope whereas the outer coil, extending over the remaining portion of the coil assembly, defines a moderate radiopacity. By way of further illustration, the guidewires of either FIGS. 1 or 2 may incorporate a flattened tip segment 30 extending from the distal end of the shaft, through the inner coil and attached, at its distal end, to the tip weld 26.

The plating in the foregoing embodiment may be gold and may vary in thickness from about 0.00005" to about 0.00015", although the thickness of the plating and type of materials used may be varied to achieve the desired radiopacity. It also should be understood that the dimensions, tapers and the like may be varied as desired to suit particular objectives, as will be appreciated by those skilled in the art.

FIG. 3 illustrates another embodiment of the invention in which a single helical coil 40 is attached to the distal region of the shaft 42 of the guidewire. The distal region 44 typically is tapered, and may be a step taper, as shown, or may assume other tapered configurations, as desired. The tapered portion of the shaft terminates short of the distal end of the coil. A safety wire 46 may extend from a point of attachment on the tapered distal region 44 of the core wire to the distal tip weld 48. In order to achieve the highly radiopaque distal portion and moderately radiopaque more proximal portion, the coil 40 may be formed from a material having a relatively low radiopacity, such as stainless steel wire, the wire being plated, as indicated at 33, with a thin plating of gold before winding the wire into a coil. The highly radiopaque distal tip portion of the coil then may be formed by electroplating the outer exposed surface of the coil further with a layer 47 of highly radiopaque material such as gold. The highly radiopaque segment preferably is between 2 and 4 cm long. In order to prevent the adjacent turns of the coil from becoming rigidly connected by the electroplated gold, the coil preferably is wound to very slightly space the adjacent turns of the coil. For example, the turns may be spaced of the order of 0.0002". In a further variation of this embodiment, illustrated in FIG. 4, the coil 40 may be formed from a non-radiopaque material, such as stainless steel and may be provided with a moderate amount of plating 49 over its full length and a heavier amount of plating 50 on its distal tip portion. Here, again, the plating preferably is gold, although other materials may be used. The plating, in this variation, may be deposited on the finished coil as by electroplating. Because of the slight spacing of the turns of the coil, some very thin electroplating may occur on the inner surfaces of the coils, although the metal so deposited is extremely thin and of inconsequential radiopacity. As with the previously described embodiments, the overall length of the guidewire may be of the order of 175 cm long with the distal tapered segment of the shaft being of the order of 30 cm long. The distal tip of the tapered segment 44 may terminate approximately 2 cm short of the distal tip of the coil, which is about 32 cm long. The shaft 42 may be of the order of 0.014" to 0.016" in diameter.

FIG. 5 illustrates a further embodiment of the invention similar in construction to the embodiment of FIG. 4 but in which the coil 40 is formed from an alloy that will display a moderate radiopacity under a fluoroscope. For example, LTC (low thermal coefficient) alloys which may have a composition of 65% gold, 25% nickel and 10% chromium may be employed for the wire of the coil. A distal segment 60 of the coil may be electroplated to further enhance the radiopacity of that segment to a degree that will display a dark image under fluoroscopy. Thus, in this embodiment, the moderate radiopacity is derived from the inherent level of radiopacity provided by the alloy from which the coil is formed and the dark distal segment is provided by the combined radiopacity of the coil alloy and the electroplating.

FIG. 6 illustrates a further embodiment (with the tapered porton of the shaft omitted for clarity of illustration) of guidewire having variable radiopaque segments in which the guidewire has a distal tip segment 62 that is highly radiopaque, an intermediate segment 64 that is non-radiopaque and a proximal segment 66 that is moderately radiopaque. The highly radiopaque distal segment 62 provides clear, visible fluoroscopic indication of the distal tip of the guidewire to indicate clearly the guidewire position. Typically, the distal tip of the guidewire is advanced through and beyond the stenosis to be treated. The intermediate, non-radiopaque segment 64 is intended to be disposed so that the region of the artery in which the stenosis is located will be completely unobstructed by any radiopaque effects of the guidewire so that the full radiopaque effect of radiopaque contrast liquid injected into the artery can be visualized on the fluoroscope, particularly in the critical region of the stenosis. The moderately radiopaque proximal segment 66 provides an indication of the position and configuration of the more proximally located portions of the guidewire, as discussed above in connection with other embodiments. The guidewire of this embodiment may have an internal construction such as that illustrated in connection with FIGS. 3 and 4, although other internal guidewire constructions may be employed, it being understood that the arrangement of a guidewire having sequentially highly radiopaque, non-radiopaque and moderately radiopaque segment may be adapted to various guidewire constructions. By way of example, in a preferred embodiment incorporating an internal construction such as that disclosed in FIGS. 3 and 4, the guidewire of this invention may have a distal segment 62 of high radiopacity of the order of 3 cm long, an intermediate non-radiopaque segment 64 of the order of 5 cm long and a moderately radiopaque proximal segment 66 approximately 28 cm long. The highly radiopaque distal segment may be formed by electroplating the distal segment as at 68 with a highly radiopaque material to a thickness that will provide the high degree of radiopacity. The plating 68 may be as described above in connection with the previous embodiments. As illustrated, a double thickness of plating may be formed over the distal segment. The proximal segment 66 may be plated as at 70 with the same plating material, the moderate radiopacity being achieved by plating it to a lesser thickness than the distal segment. Thus, the proximal segment is illustrated as having a single thickness of electroplating, although it should be understood that the illustration of single and double thicknesses for purposes of illustration only. The intermediate non-radiopaque segment results from omitting plating from the intermediate segment. This may be achieved by masking the intermediate segment 64 with an appropriate material such as a film of lacquer or varnish before electroplating the coil, then electroplating the distal segment 62 for a longer period of time than the electroplating of the proximal segment 66. After the coil has been plated, the masking may be stripped away from the intermediate segment 64. Alternately, the coil may be electroplated first at the proximal segment 66 and then separately at the distal segment 62, with the distal segment receiving a heavier thickness of electroplating. Thus, the coil, being formed from a relatively non-radiopaque material, such as stainless steel, the intermediate segment 64 will appear relatively non-radiopaque under the fluoroscope and will enable the intermediate portion of the guidewire to be disposed within the stenosis to facilitate fluoroscopic visualization of the stenosis when contrast liquid is injected into the artery.

Thus, we have described a guidewire having varied degrees of radiopacity whereby a proximal portion of the distal region of the guidewire presents a moderately shadowed appearance under fluoroscopy and the more distal portion is highly radiopaque. It should be understood, however, that the foregoing description of the invention is intended merely to be illustrative thereof and that other embodiments and modifications may be apparent to those skilled in the art without departing from its objects, purposes and spirit.

Having thus described the invention what we desire to claim and secure by Letters Patent is:

1. A guidewire comprising:
   an elongate flexible shaft;
   an elongate helical outer coil attached to the distal portion of the shaft and receiving a distal region of the shaft within the coil, the distal end of the shaft terminating short of the distal end of the coil;
   that portion of the shaft that is contained within the outer coil being plated with a highly radiopaque material;
   an inner helical coil having a smaller diameter than the inner diameter of the outer coil, the inner coil being attached at its proximal end to the distal end of the shaft and, at its distal end, to a tip weld, the distal end of the outer coil also being attached to the tip weld;
   the inner coil being formed from a highly radiopaque material;
   whereby when viewed under fluoroscopy the proximal portion of the distal region will appear moderately radiopaque as compared to the more distal portion of the distal region which will appear highly radiopaque.

2. A guidewire as defined in claim 1 further comprising a thin wire element extending within the inner helical coil between the distal end of the shaft and the tip weld.

3. A guidewire comprising:
   an elongate flexible shaft;
   an elongate helical coil attached to the distal portion of the shaft and receiving a distal region of the shaft within the coil, the distal end of the shaft terminating short of the distal end of the coil;
   the wire of the coil being formed from a relatively non-radiopaque material and being plated with a thin plating of a highly radiopaque material, the distal portion of the coil being further plated with a highly radiopaque material along a distal segment of the coil whereby when viewed under fluoroscopy, the proximal portion of the coil will appear moderately radiopaque as compared to the more distal portion of the coil which will appear highly radiopaque.

4. A guidewire comprising:
   an elongate flexible shaft;
   an elongate helical coil attached to the distal portion of the shaft and receiving a distal region of the shaft within the coil, the distal end of the shaft terminating short of the distal end of the coil;
   the coil being formed from a non-radiopaque material, the coil being plated with a moderately radiopaque plating along its proximal portion and with a heavier plating of radiopaque material at its distal tip whereby when viewed under fluoroscopy, the proximal portion of the distal region of the coil will appear moderately radiopaque as compared to the more distal portion of the helical coil which will appear highly radiopaque.

5. A guidewire comprising:
   an elongate flexible shaft;

an elongate helical coil attached to the distal portion of the shaft and receiving a distal region of the shaft within the coil;

the coil being constructed as to have a highly radiopaque distal segment, a relatively non-radiopaque intermediate segment and a relatively moderately radiopaque proximal segment.

6. A guidewire as defined in claim 5 further comprising:

the coil being formed from a non-radiopaque material, the coil being relatively heavily plated in the distal segment, being moderately plated at the proximal segment and being relatively free of plating at the intermediate segment.

* * * * *